(12) United States Patent
Kitko et al.

(10) Patent No.: US 8,936,796 B2
(45) Date of Patent: *Jan. 20, 2015

(54) HAIR CARE COMPOSITIONS COMPRISING SUCROSE POLYESTERS

(75) Inventors: David Johnathan Kitko, Cincinnati, OH (US); Howard David Hutton, III, Oregonia, OH (US); Jorge Max Sunkel, Cincinnati, OH (US); Elaine Marie Burt, Cincinnati, OH (US); Marcela Victoria Valenzuela, West Chester, OH (US)

(73) Assignee: The Procter & Gamble Company, CIncinnati, OH (US)

( * ) Notice: Subject to any disclaimer, the term of this patent is extended or adjusted under 35 U.S.C. 154(b) by 257 days.

This patent is subject to a terminal disclaimer.

(21) Appl. No.: 12/391,599

(22) Filed: Feb. 24, 2009

(65) Prior Publication Data

US 2009/0246236 A1    Oct. 1, 2009

Related U.S. Application Data

(60) Provisional application No. 61/031,172, filed on Feb. 25, 2008.

(51) Int. Cl.
| A61K 8/02 | (2006.01) |
|---|---|
| A61K 8/00 | (2006.01) |
| A61Q 5/02 | (2006.01) |
| A61K 8/34 | (2006.01) |
| A61K 8/73 | (2006.01) |
| A61K 8/85 | (2006.01) |

(52) U.S. Cl.
CPC . *A61Q 5/02* (2013.01); *A61K 8/342* (2013.01); *A61K 8/73* (2013.01); *A61K 8/731* (2013.01); *A61K 8/737* (2013.01); *A61K 8/85* (2013.01); *A61K 5/12* (2013.01); *A61K 2800/5426* (2013.01); *A61K 2800/594* (2013.01)
USPC .......................................... 424/401; 424/70.1

(58) Field of Classification Search
None
See application file for complete search history.

(56) References Cited

U.S. PATENT DOCUMENTS

| 5,705,147 | A | 1/1998 | Shapiro |
|---|---|---|---|
| 5,843,881 | A | 12/1998 | Dubois |
| 5,916,575 | A | 6/1999 | McAtee |
| 5,951,991 | A | 9/1999 | Wagner |
| 5,972,361 | A | 10/1999 | Fowler |
| 5,980,931 | A | 11/1999 | Fowler |
| 6,004,915 | A | 12/1999 | Elliott |
| 6,063,997 | A | 5/2000 | Endo |
| 6,126,930 | A | 10/2000 | Dubois |
| 6,132,746 | A | 10/2000 | Hasenoehrl |
| 6,217,889 | B1 | 4/2001 | Lorenzi |
| 6,267,975 | B1 | 7/2001 | Smith, III |
| 6,284,802 | B1 | 9/2001 | Bissett |
| 6,303,119 | B1 | 10/2001 | Weisgerber |
| 6,322,801 | B1 | 11/2001 | Lorenzi |
| 6,350,441 | B1 | 2/2002 | Giles |
| 6,410,017 | B1 | 6/2002 | Weisgerber |
| 6,428,779 | B1 | 8/2002 | Sauermann |
| 6,440,439 | B1 | 8/2002 | Giles |
| 6,491,928 | B1 | 12/2002 | Smith, III |
| 6,569,663 | B1 | 5/2003 | Rubingh |
| 6,638,519 | B1 | 10/2003 | Lorant |
| 6,677,294 | B2 | 1/2004 | Shaw |
| 6,706,674 | B2 | 3/2004 | Cincotta |
| 6,908,757 | B1 | 6/2005 | Rubingh |
| 6,955,817 | B2 | 10/2005 | McAtee |
| 7,087,560 | B2 | 8/2006 | McManus |
| 7,115,535 | B1 | 10/2006 | Smith, III |
| 7,115,551 | B2 | 10/2006 | Hasenoehrl |
| 7,119,057 | B2 | 10/2006 | Popplewell |
| 7,122,512 | B2 | 10/2006 | Brain |
| 2001/0055599 | A1 | 12/2001 | Drzewiecki |
| 2002/0006886 | A1 | 1/2002 | Beerse |
| 2002/0012645 | A1 | 1/2002 | Midha |
| 2002/0168327 | A1 | 11/2002 | Bailey |
| 2003/0143178 | A1 | 7/2003 | Komure |
| 2003/0180242 | A1 | 9/2003 | Eccard et al. |

(Continued)

FOREIGN PATENT DOCUMENTS

| EP | 935456 A1 | 8/1999 |
|---|---|---|
| EP | 941057 A1 | 9/1999 |
| EP | 952809 A1 | 11/1999 |
| EP | 973483 A1 | 1/2000 |
| EP | 983048 A1 | 3/2000 |
| EP | 1032355 A1 | 9/2000 |
| EP | 1051149 A1 | 11/2000 |
| EP | 946129 B1 | 8/2001 |
| EP | 952808 B1 | 8/2001 |
| EP | 1227790 A1 | 8/2002 |
| EP | 1317241 A2 | 6/2003 |

(Continued)

OTHER PUBLICATIONS

Sefose 2275 MSDS, retrieved online on May 17, 2011.*

(Continued)

*Primary Examiner* — Blessing M Fubara
*Assistant Examiner* — Jennifer A Berrios
(74) *Attorney, Agent, or Firm* — James T. Fondriest

(57) ABSTRACT

A hair care composition having a conditioning active comprising a sucrose polyester having a melting point greater than about 30° C., an IBAR greater than about 5, an IV of about 3 to about 70, and an aqueous carrier, and may further comprise optional ingredients including but not limited to, silicone, cationic polymers, and fatty alcohols. The composition can also comprise a blend of sucrose polyesters, wherein the blend comprises two or more sucrose polyesters, wherein at least one sucrose polyester has a melting point greater than about 30° C., an IBAR greater than about 5, an IV of about 3 to about 70, and at least one sucrose polyester has an IBAR between about 1 and about 8, and an IV between about 1 and about 135, and wherein the sucrose polyester blend has an IBAR of at least 5 and an IV of about 1 and about 135.

8 Claims, 1 Drawing Sheet

(56) References Cited

U.S. PATENT DOCUMENTS

| | | |
|---|---|---|
| 2003/0186826 A1 | 10/2003 | Eccard et al. |
| 2003/0199404 A1 | 10/2003 | Lorenzi et al. |
| 2003/0223952 A1 | 12/2003 | Wells et al. |
| 2003/0228352 A1 | 12/2003 | Hasenoehrl et al. |
| 2004/0042991 A1 | 3/2004 | Klug |
| 2004/0120918 A1 | 6/2004 | Lintner |
| 2004/0180027 A1 | 9/2004 | Kumar |
| 2004/0208903 A1 | 10/2004 | Robinson et al. |
| 2004/0235693 A1 | 11/2004 | Wei et al. |
| 2004/0242097 A1 | 12/2004 | Hasenoehrl et al. |
| 2004/0248748 A1 | 12/2004 | Wei et al. |
| 2004/0253297 A1 | 12/2004 | Hedges et al. |
| 2004/0254086 A1 | 12/2004 | Hedges et al. |
| 2004/0258645 A1 | 12/2004 | Trejo et al. |
| 2005/0008604 A1 | 1/2005 | Schultz et al. |
| 2005/0152864 A1 | 7/2005 | Watanabe |
| 2005/0232892 A1 | 10/2005 | Banks |
| 2005/0238680 A1 | 10/2005 | Stella |
| 2005/0239670 A1 | 10/2005 | Stella |
| 2005/0255059 A1 | 11/2005 | Oblong |
| 2005/0255075 A1 | 11/2005 | Meder |
| 2005/0276829 A1 | 12/2005 | Stella |
| 2006/0024256 A1 | 2/2006 | Wells |
| 2006/0235370 A1 | 10/2006 | Oblong et al. |
| 2006/0263309 A1 | 11/2006 | Bissett et al. |
| 2006/0269502 A1 * | 11/2006 | Johnson et al. ............ 424/70.13 |
| 2006/0275228 A1 | 12/2006 | Bissett et al. |
| 2007/0027051 A1 | 2/2007 | Staudigel |
| 2007/0110696 A1 | 5/2007 | Johnson |
| 2007/0184007 A1 | 8/2007 | Walter |
| 2007/0196292 A1 | 8/2007 | Robinson et al. |

FOREIGN PATENT DOCUMENTS

| | | | |
|---|---|---|---|
| EP | 1289487 | B1 | 12/2006 |
| JP | 06264049 | A | 9/1994 |
| JP | 2004161705 | A | 6/2004 |
| JP | 2006056785 | | 3/2006 |
| WO | WO9804241 | A2 | 2/1998 |
| WO | WO9924010 | A1 | 5/1999 |
| WO | WO0100168 | A1 | 1/2001 |
| WO | WO0217865 | * | 3/2002 |
| WO | 2008063471 | A2 | 5/2008 |

OTHER PUBLICATIONS

Sefose Product Sheet, retrieved online May 17, 2011.*

XP002533982; PG Chemicals, Delivering Solutions, Creating Value, retrieved from the internet on Jun. 25, 2009.

* cited by examiner

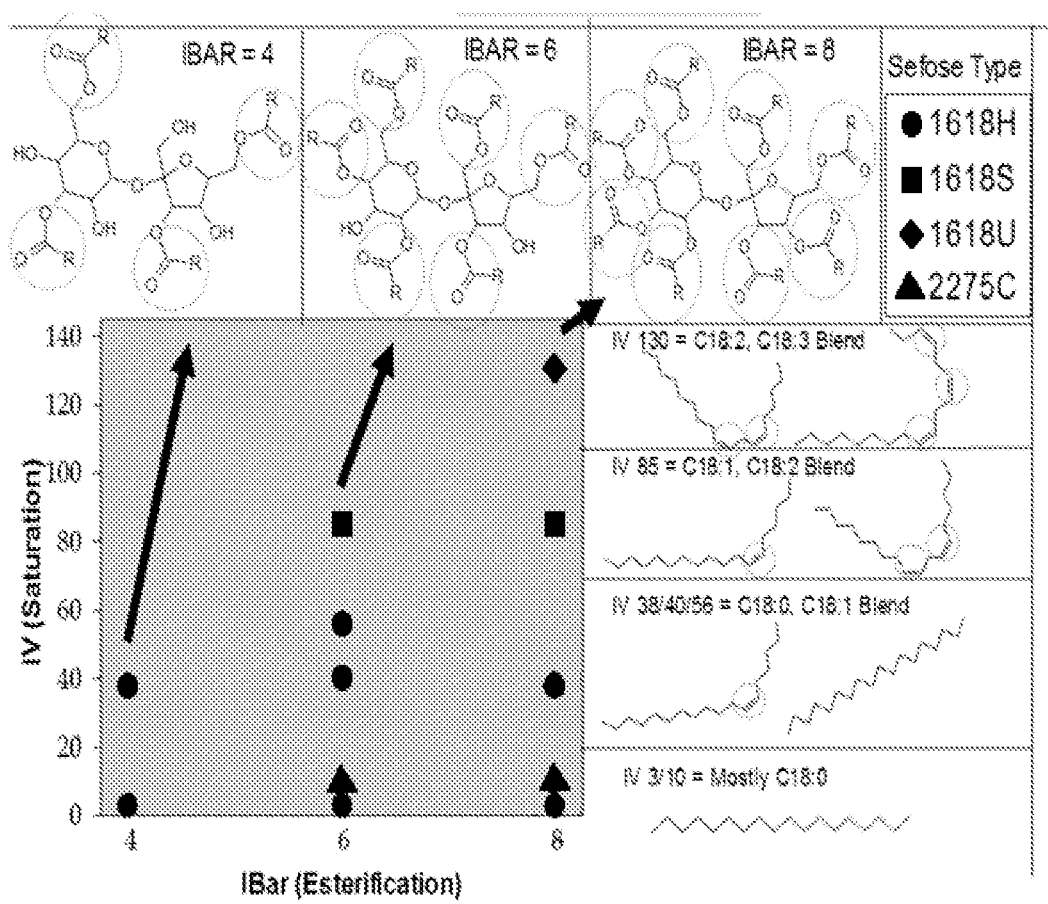

HAIR CARE COMPOSITIONS COMPRISING SUCROSE POLYESTERS

CROSS REFERENCE TO RELATED APPLICATION

This application claims the benefit of U.S. Provisional Application No. 61/031,172, filed Feb. 25, 2008.

FIELD OF THE INVENTION

The present invention relates to hair care compositions for delivering a conditioning benefit, comprising sucrose polyesters.

BACKGROUND OF THE INVENTION

Human hair becomes dry and/or damaged due to the surrounding environment, styling, drying, and/or coloring or otherwise chemically treating the hair.

A variety of approaches have been developed to condition the hair. A common method of providing conditioning benefit is through the use of hair care compositions containing conditioning agents such as cationic surfactants and polymers, high melting point fatty compounds, low melting point oils, silicone compounds, and mixtures thereof. Silicones are often used as a conditioning active for a number of hair care compositions. However, the rising costs, the inefficient conditioning of damaged hair, and the petroleum based nature of silicone has minimized its desirability as a conditioning active.

Based on the foregoing, there is a need for a conditioning active which can provide conditioning benefits to hair which can replace, or be used in combination with silicone, or other conditioning active, to maximize the conditioning activity of a hair care composition. Additionally, there is a need to find a conditioning active which can deliver a conditioning benefit to damaged hair, which has previously been difficult to condition using traditional conditioning actives. Finally, there is a need to find a conditioning active which can be derived from a natural source, thereby providing a conditioning active derived from a renewable resource.

None of the existing art provides all of the advantages and benefits of the present invention.

SUMMARY OF THE INVENTION

The present invention relates to a hair care composition comprising: a conditioning active comprising a sucrose polyester having a melting point greater than about 30° C., an IBAR greater than about 5, an IV of about 3 to about 70; a fatty alcohol having from about 14 to about 30 carbon atoms; and an aqueous carrier.

Another embodiment of the present invention is a hair care composition comprising: a conditioning active comprising a sucrose polyester blend, wherein the blend comprises two or more sucrose polyesters, wherein at least one sucrose polyester has a melting point greater than about 30° C., an IBAR greater than about 5, an IV of about 3 to about 70, and at least one sucrose polyester has an IBAR between about 1 and about 8, and an IV between about 1 and about 135, and wherein the sucrose polyester blend has an IBAR of at least 5 and an IV of about 1 and about 135; and an aqueous carrier.

Another embodiment of the present invention is a hair care composition comprising: a conditioning active comprising a sucrose polyester having a melting point greater than about 30° C., an IBAR greater than about 5, and an IV of about 3 to about 70; a cationic polymer; and an aqueous carrier Yet another embodiment of the present invention is a hair care composition comprising: a combination of conditioning active comprising an insoluble silicone, a sucrose polyester having a melting point greater than about 30° C., an IBAR greater than about 5, an IV of about 3 to about 70; a cationic polymer; and an aqueous carrier.

These and other features, aspects, and advantages of the present invention will become evident to those skilled in the art from a reading of the present disclosure.

BRIEF DESCRIPTION OF THE DRAWINGS

While the specification concludes with claims which particularly point out and distinctly claim the present invention, it is believed that the present invention will be better understood from the following description of embodiments, taken in conjunction with the accompanying drawings, in which like reference numerals identify identical elements and wherein:

FIG. 1 is graph indicating IBAR and IV values for sucrose polyesters.

DETAILED DESCRIPTION OF THE INVENTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

The term "charge density", as used herein, refers to the ratio of the number of positive charges on a polymer to the molecular weight of said polymer.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the elements and limitations of the invention described herein, as well as any of the additional or optional ingredients, components, steps, or limitations described herein.

The term "hair care composition" as used herein shall include shampoos, rinse out conditioners, leave in conditioners, styling products, and/or hair colorants.

The term "polymer" as used herein shall include materials whether made by polymerization of one type of monomer or made by two (i.e., copolymers) or more types of monomers.

The term "shampoo" as used herein means a composition for cleansing and conditioning hair or skin, including scalp, face, and body.

The term "suitable for application to human hair" as used herein means that the compositions or components thereof so described are suitable for use in contact with human hair and the scalp and skin without undue toxicity, incompatibility, instability, allergic response, and the like.

The hair care compositions of the present invention comprise at least one conditioning active, wherein the conditioning active comprises a sucrose polyester. The conditioning active may further comprise an insoluble silicone.

The hair care composition of the present invention can deliver a consumer noticeable conditioning benefit. In particular the hair care composition of the present invention delivers both wet and dry conditioning benefits, as indicated by wet/dry combing test data. Additionally, the hair care composition of the present invention may deliver conditioning to damaged hair which has traditionally been difficult to achieve. Additionally, the hair care composition of the present invention delivers a different, cleaner and/or lighter softness than traditional silicones. Each of these components, as well as other relevant components, is described in detail hereinafter.

I. Sucrose Polyesters

The hair care compositions of the present invention comprise one or more types of sucrose polyesters (also referred to herein as "Sefose"). Sucrose polyesters are derived from a natural resource and therefore, the use of sucrose polyesters as the conditioning active can result in a positive environmental impact.

Sucrose polyesters are polyester materials, having multiple substitution positions around the sucrose backbone coupled with the chainlength, saturation, and derivation variables of the fatty chains. The Sucrose polyesters display both a range of esterification and saturation as shown in FIG. 1.

The sucrose polyester of the present invention have an esterification ("IBAR") of greater than about 5. In one embodiment the sucrose polyester may have an IBAR of from about 5 to about 8. In another embodiment the sucrose polyester has an IBAR of about 5-7, and in another embodiment the sucrose polyester has an IBAR of about 6. In yet another embodiment the sucrose polyester has an IBAR of about 8. As the sucrose polyesters are derived from a natural resource, a distribution in the IBAR and chain length may exist. For example a sucrose polyester having an IBAR of 6, may contain a mixture of mostly IBAR of about 6, with some IBAR of about 5 and some IBAR of about 7. Additionally, the sucrose polyester of the present invention may have a saturation or iodine value ("IV") of about 3 to about 70. In another embodiment the sucrose polyester of the present invention may have an IV of about 3. In yet another embodiment the sucrose polyester of the present invention may have an IV of about 40. The sucrose polyesters of the present invention may have a melting point greater than about 30° C. Further, the sucrose polyesters of the present invention has a chain length of about C12 to C14, and may comprise some C16, for the sucrose polyesters having an IBAR of about 5 to about 7. For the sucrose polyesters having an IBAR of about 8, the chain length is about C16 to C18.

In yet another embodiment the conditioning active can comprise a blend of more than one sucrose polyester. This sucrose polyester blend can comprise two or more sucrose polyesters, wherein at least one sucrose polyester has a melting point greater than about 30° C., an IBAR greater than about 5, an IV of about 3 to about 70, and at least one sucrose polyester has an IBAR between about 1 and about 8, and an IV between about 1 and about 135, and wherein the sucrose polyester blend has an IBAR of at least 5 and an IV of about 1 and about 135. In one embodiment the sucrose polyester blend can be at a ratio of about 1:1, in another embodiment the sucrose polyester blend can be at a ratio of about 1:2, in yet another embodiment the sucrose polyester can be at a ratio of about 1:3, in yet another embodiment the sucrose polyester can be at a ratio of about 1:5, in yet another embodiment the sucrose polyester can be at a ratio of about 3:4, and in yet another embodiment the sucrose polyester can be at a ratio of about 3:10 of the sucrose polyester having a melting point greater than about 30° C., an IBAR greater than about 5, an IV of about 3 to about 70 to the sucrose polyester having an IBAR between about 1 and about 8, and an IV between about 1 and about 135. In one embodiment the sucrose polyester blends can have a G' value of from about 0.22 Pa to about 10,030 Pa at 0.01 Hz. Additionally, in one embodiment the sucrose polyester blends can have a G" value of from about 0.83 Pa to about 23,960 at about 0.01 Hz.

Table 1 reports the average values of G' and G" from 0.01 Hz, up to 100 Hz, for varying blends of a sucrose polyester having a melting point greater than about 30° C., an IBAR greater than about 5, an IV of about 3 to about 70 (Sefose 1618H, P&G Chemicals) with a sucrose polyester having an IBAR between about 1 and about 8, and an IV between about 1 and about 135 (Sefose 1618U, P&G Chemicals). The blends are prepared by placing the amounts and types of sucrose polyesters, at the specified ratio, in a stainless steel beaker which is heated in a water bath at about 75° C. At this temperature any solid sucrose polyester present in the blend melted and is intimately mixed with all other sucrose polyester to create a homogenous mixture. After this, the beaker is removed from the bath and allowed to cool at room temperature. Samples from these blends are transferred to the rheometer for G' and G" measurements.

TABLE 1

| | Sefose 1618H to Sefose 1618U Ratio | | | | | | | | | |
|---|---|---|---|---|---|---|---|---|---|---|
| Freq. | 1:1 | | 3:4 | | 1:2 | | 3:10 | | 1:5 | |
| Hz | G' Pa | G" Pa | G' Pa | G" Pa | G' Pa | G" Pa | G' Pa | G" Pa | G' Pa | G" Pa |
| 0.01 | 10030 | 23960 | 23.9 | 29.3 | 1.17 | 4.51 | 0.57 | 1.42 | 0.22 | 0.83 |
| 0.1 | 9911 | 68360 | 24.6 | 46.6 | 4.61 | 11.9 | 1.26 | 3.62 | 0.74 | 2.64 |
| 1 | 56110 | 394800 | 73.2 | 224.7 | 14.5 | 55.1 | 3.20 | 19.0 | 2.25 | 15.9 |
| 10 | — | — | 514.3 | 1226 | 98.9 | 341.6 | 15.9 | 159.0 | 52.7 | 141.9 |
| 100 | — | — | 47750 | 17740 | 78070 | 13390 | 54400 | 8958 | 64670 | 17010 |

Examples of sucrose polyesters suitable for use in the present invention include, but are not limited to, Sefose 1618H, Sefose 2275 C, 1618S all available from The Procter and Gamble Co. of Cincinnati, Ohio.

The following data (shown in Table 2) shows that sucrose polyesters having the abovementioned characteristics deliver dry combing benefits, which correlates to conditioning, that exceed the dry combing benefits of sucrose polyesters that do not have the abovementioned characteristics. For example Sefose C1618 IB6 IV85, has lower dry combing benefits than Sefose C1618 IB6 IV40 and IV 56, and Sefose C1618 IB6 IV3. Additionally, Sefose C1618 IB8 IV 135, and Sefose C1618 IB8 IV85 have lower dry combing benefits than Sefose C1618 IB8 IV38, Sefose C2275 IB8 IV5 and Sefose C1618 IB8 IV3.

TABLE 2

Low Lift Hair Dry Comb Ease - Body

|  | Mean | 95% LSD | | | |
|---|---|---|---|---|---|
| IBar 6 | | | | | |
| Clarifying base | 1.00000 | A | | | |
| Sefose C1618 IB6 IV85 in clarifying base | 3.42857 | | B | | |
| Sefose C1618 IB6 IV40 in clarifying base | 4.92857 | | B | C | |
| Sefose C1618 IB6 IV56 in clarifying base | 5.42857 | | | C | D |
| Sefose C1618 IB6 IV3 in clarifying base | 5.57143 | | | C | D |
| Si in clarifying base | 6.85714 | | | | D |
| Clarifying/Si Conditioner | 9.28571 | | | | | E |
| IBar 8 | | | | | |
| Clarifying base | 1.50000 | A | | | |
| Sefose C1618 IB8 IV135 in clarifying base | 2.75000 | A | B | | |
| Sefose C1618 IB8 IV85 in clarifying base | 3.00000 | A | B | | |
| Si in clarifying base | 6.37500 | | | | D |
| Clarifying/Si Conditioner | 9.37500 | | | | | E |
| Clarifying base | 1.37500 | A | | | |
| Si in clarifying base | 4.50000 | | B | | |
| Sefose C1618 IB8 IV38 in clarifying base | 5.50000 | | B | C | |
| Sefose C2275 IB8 IV5 in clarifying base | 5.62500 | | B | C | |
| Sefose C1618 IB8 IV3 in clarifying base | 5.75000 | | B | C | |
| Clarifying/Si Conditioner | 9.25000 | | | | D |

In addition to use in hair care compositions, sucrose polyesters of the present invention may be beneficial as a conditioning agent in personal care compositions, in particular personal cleansing compositions such as a body wash.

Conditioning Benefit

Silicone does not traditionally condition damaged or low lift hair as efficiently as silicone conditions undamaged hair. Low lift hair includes hair that has been exposed to bleaching or other coloring agents. Hair care formulations, in particular shampoo formulations, comprising the sucrose polyester of the present invention work well alone or in combination with silicone conditioning actives to deliver improved dry combing benefits to damaged or low lift hair. Adding silicone, and in particular small particle silicone, adds to the combing benefit. The silicone and sefose do not counteract each other. The following Tables 3-4 indicate that Sefose in a clarifying shampoo base has better dry combing benefit (which correlates to a conditioning benefit) than a clarifying shampoo alone, for both low lift and virgin brown hair. Additionally, Tables 3-4 below indicate that Sefose combined with small particle silicone in a clarifying shampoo base is nearly equivalent in dry combing benefit to Clarifying/Si Conditioner which is a conditioner for low lift hair, and is equivalent in dry combing benefit to Clarifying/Si Conditioner for virgin brown hair. See Tables 5-7 for formulations described in Tables 3-4.

TABLE 3

C12 IB6 IV1 and C1618, IBar6 - IV40 and above deliver dry combing benefits vs. Silicone alone

|  | Mean | 95% LSD | | | |
|---|---|---|---|---|---|
| C12 IB6 - Low Lift Hair | | | | | |
| Clarifying | 1.62500 | A | | | |
| Sefose C1214 IB6 IV1 | 4.37500 | | B | | |
| Si | 4.37500 | | B | | |
| Sefose C1295 IB6 IV1 | 4.62500 | | B | | |
| Sefose C1214 IB6 IV1 + Si | 6.50000 | | | C | D |
| Sefose C1295 IB6 IV1 + Si | 6.75000 | | | | D |
| Clarifying/Si Conditioner Low Lift Hair | 9.50000 | | | | | E |
| Clarifying | 0.87500 | A | | | |
| Si | 5.25000 | | B | | |
| Sefose C1618 IB6 IV56 + Si | 7.12500 | | | C | |
| Sefose C1618 IB6 IV40 + Si | 7.28571 | | | C | |
| Clarifying/Si Conditioner | 9.50000 | | | | D |
| Large and Small particle Si - Virgin Brown Hair | | | | | |
| Clarifying | 1.25000 | A | | | |
| Clarifying + guar | 1.87500 | A | | | |
| Si (large particle) | 4.37500 | | B | | |
| Sefose C1618 IB6 IV40 | 5.18800 | | B | | |
| Sefose C1618 IB6 IV40 + Si (large particle) | 7.50000 | | | C | |
| Si (small particle) | 7.93800 | | | C | D |
| Sefose C1618 IB6 IV40 + Si (small particle) | 8.81300 | | | | D |
| Clarifying/Si Conditioner | 9.18800 | | | | D |

TABLE 4

|  | Mean | 95% LSD | | |
|---|---|---|---|---|
| Compact shampoo | 2.375 | X | | |
| Sefose C1618 IB8 IV3 in compact shampoo | 6.250 | X | | |
| Sefose C1618 IB6 IV40 in compact shampoo | 6.313 | X | | |
| Silicone in compact shampoo | 6.750 | X | X | |
| Sefose C1618 IB6 IV40 + Si in compact shampoo | 8.188 | | X | X |
| Shampoo + Conditioner | 9.500 | | | X |

TABLE 5

Clarifying/Si Conditioner Formula

| L-Glutamic Acid | 0.640 |
|---|---|
| Stearamidoproplydimethylamine | 2.0 |
| Cetyl Alcohol | 2.5 |
| Stearyl Alcohol | 4.5 |
| Dimethicone/Cyclomethicone (15/85 Blend) | 4.2 |
| Ethylene Diamine Tetraacetic Acid | 0.1 |
| Benzyl Alcohol | 0.4 |
| Kathon CG | 0.33 |
| Perfume | 0.25 |
| dl-Pantyl | 0.225 |
| dl-Panthenol | 0.05 |

TABLE 6

Typical Clarifying Shampoo Formulation

| Raw Material | % (wt./wt.) |
|---|---|
| Distilled Water | Qs |
| SLE3S | 7.0000 |
| tetrasodium EDTA | 0.1400 |
| Citric Acid (Anhy.) | 1.1100 |
| Sodium Citrate (dihydrate) | 0.0000 |
| Cocamide MEA | 0.5000 |
| Kathon CG | 0.0300 |
| SLS | 7.0000 |
| DMDM Hydantoin | 0.1000 |
| cocoamidopropyl betaine | 2.0000 |
| Cocamide MEA | 0.5 |
| NaCl | 0.7000 |
| Perfume | 0.4600 |
| Total | 100.0000 |

TABLE 7

| Compact Shampoo Formula Ingredient | Targ. wt % |
|---|---|
| SLE1S | 12.400 |
| SLE1S (conc 70%) | 4.000 |
| CB | 2.200 |
| C11S | 5.000 |
| N67S | 1.000 |
| EDTA | 0.100 |
| Sodium Citrate | 0.400 |
| Na EGDS mix | 1.250 |
| Kathon CG | 0.00005 |
| Citric Acid | pH 5.5-6.5 |
| Guar | 0.2 |
| Silicone (when added) | 2.7 |
| Sefose (when added) | 2.7 |
| Water | q.s. |

II. Shampoo Formulations

Shampoo formulations of the present invention incorporate sucrose polyesters via either pre-emulsification or crystallization in-situ at different cooling rates from a hot melt formulation. Incorporation of the sucrose polyesters of the present invention deliver both conditioning benefits parity to traditional conditioning actives such as silicone, as evidenced by combing test results. The shampoo formulations comprise sucrose polyester particles of a size from about 0.05 to about 35 microns. In one embodiment the sucrose polyester particles are from about 0.1 to about 10 microns. In another embodiment the sucrose polyester particles are from about 0.3 to about 10 microns. In another embodiment the sucrose polyester particles are from about 0.5 to about 2 microns. In yet another embodiment the sucrose polyester particles are from about 10 to about 35 microns, and in yet another embodiment the sucrose polyester particles are about one micron. The shampoo formulations may further comprise one or more optional ingredient(s).

Shampoo Formulation Optional Ingredients

A. Detersive Surfactant

The composition of the present invention includes a detersive surfactant. The detersive surfactant component is included to provide cleaning performance to the composition. The detersive surfactant component in turn comprises anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the composition herein include those which are known for use in hair care or other personal care cleansing compositions. The concentration of the anionic surfactant component in the composition should be sufficient to provide the desired cleaning and lather performance, and generally range from about 5% to about 50%, preferably from about 12% to about 40%, preferably from about 8% to about 30%, more preferably from about 10% to about 25%, even more preferably from about 12% to about 22%.

Preferred anionic surfactants suitable for use in the compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $[R^1-SO_3-M]$ where $R^1$ is a straight or branched chain, saturated, aliphatic hydrocarbon radical having from about 8 to about 24, preferably about 10 to about 18, carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic detersive surfactants suitable for use in the compositions are the beta-alkyloxy alkane sulfonates. These surfactants conform to the formula

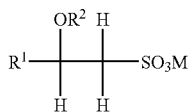

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Concentration of such amphoteric detersive surfactants preferably ranges from about 0.5% to about 20%, preferably from about 1% to about 10%. Non limiting examples of suitable zwitterionic or amphoteric surfactants are described in U.S. Pat. Nos. 5,104,646 (Bolich Jr. et al.), 5,106,609 (Bolich Jr. et al.).

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438, 091; 2,528,378.

B. Dispersed Particles

The compositions may optionally comprise particles. The particles may be dispersed water-insoluble particles. The particles may be inorganic, synthetic, or semi-synthetic. It is preferable to incorporate no more than about 20%, more preferably no more than about 10% and even more preferably no more than 2%, by weight of the composition, of particles. In one embodiment, the particles have an average mean particle size of less than about 300 μm.

Non-limiting examples of inorganic particles include colloidal silicas, fumed silicas, precipitated silicas, silica gels, magnesium silicate, glass particles, talcs, micas, sericites, and various natural and synthetic clays including bentonites, hectorites, and montmorillonites.

Examples of synthetic particles include silicone resins, poly(meth)acrylates, polyethylene, polyester, polypropylene, polystyrene, polyurethane, polyamide (e.g., Nylon®), epoxy resins, urea resins, acrylic powders, and the like.

Non-limiting examples of hybrid particles include sericite & crosslinked polystyrene hybrid powder, and mica and silica hybrid powder.

C. Aqueous Carrier

The compositions of the present invention are typically in the form of pourable liquids (under ambient conditions). The compositions will therefore typically comprise an aqueous carrier, which is present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

D. Additional Components

The compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10%.

Non-limiting examples of optional components for use in the composition include cationic polymers (guar, cationic *cassia*), conditioning agents (hydrocarbon oils, fatty esters, silicones), anti dandruff agents, suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, vitamins, niacinamide, caffeine and minoxidil.

E. Cationic Polymers

The compositions of the present invention may contain a cationic polymer. Concentrations of the cationic polymer in the composition typically range from about 0.05% to about 3%, preferably from about 0.075% to about 2.0%, more preferably from about 0.1% to about 1.0%. Preferred cationic polymers will have cationic charge densities of at least about 0.5 meq/gm, in another embodiment at least about 0.9 meq/gm, in another embodiment at least about 1.2 meq/gm, in yet another embodiment at least about 1.5 meq/gm, but in one embodiment also less than about 7 meq/gm, and in another embodiment less than about 5 meq/gm, at the pH of intended use of the composition, which pH will generally range from about pH 3 to about pH 9, in one embodiment between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, in one embodiment between about 50,000 and about 5 million, and in another embodiment between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. These preferred monomers conform the to the formula

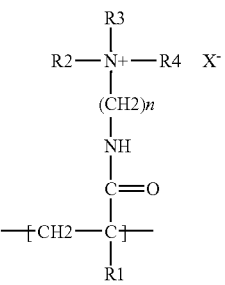

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the formula

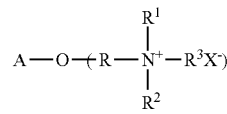

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable polymers include synthetic polymers such as those disclosed in U.S. Publication No. 2007/0207109A1. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

F. Nonionic polymers

Polyalkylene glycols having a molecular weight of more than about 1000 are useful herein. Useful are those having the following general formula:

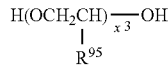

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

G. Conditioning Agents

In addition to the sucrose polyester conditioning agents described above, other conditioning agents, and in particular silicones, may be included in the hair care composition. Conditioning agents include any material which is used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. Nos. 34,584, 5,104,646, and 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, more preferably from about 100,000 to about 1,500,000 csk.

The dispersed silicone conditioning agent particles typically have a number average particle diameter ranging from about 0.01 μm to about 50 μm. For small particle application to hair, the number average particle diameters typically range from about 0.01 μm to about 4 μm, preferably from about 0.01

μm to about 2 μm, more preferably from about 0.01 μm to about 0.5 μm. For larger particle application to hair, the number average particle diameters typically range from about 4 μm to about 50 μm, preferably from about 6 μm to about 30 μm, more preferably from about 9 μm to about 20 μm, more preferably from about 12 μm to about 18 μm.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

a. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (III):

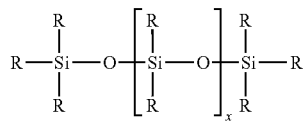

wherein R is aliphatic, preferably alkyl or alkenyl, or aryl, R can be substituted or unsubstituted, and x is an integer from 1 to about 8,000. Suitable R groups for use in the compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Preferred alkyl and alkenyl substituents are $C_1$ to $C_5$ alkyls and alkenyls, more preferably from $C_1$ to $C_4$, more preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, more preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described herein.

b. Amino and Cationic Silicones

Compositions of the present invention include an aminosilicone. Aminosilicones, as provided herein, are silicones containing at least one primary amine, secondary amine, tertiary amine, or a quaternary ammonium group. Preferred aminosilicones may have less than about 0.5% nitrogen by weight of the aminosilicone, more preferably less than about 0.2%, more preferably still, less than about 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present invention.

Preferably, the aminosilicones used in the present invention have a particle size of less than about 50μ once incorporated into the final composition. The particle size measurement is taken from dispersed droplets in the final composition. Particle size may be measured by means of a laser light scattering technique, using a Horiba model LA-910 Laser Scattering Particle Size Distribution Analyzer (Horiba Instruments, Inc.).

In one of the preferred embodiments, the aminosilicone has a viscosity of from about 1,000 cs (centistokes) to about 1,000,000 cs, more preferably from about 10,000 cs to about 700,000 cs, more preferably from about 50,000 cs to about 500,000 cs, and still more preferably from about 100,000 cs to about 400,000 cs. This embodiment may also comprises a low viscosity fluid, such as, for example, those materials described below in Section F.(1). The viscosity of aminosilicones discussed herein is measured at 25° C.

In another preferred embodiment, the aminosilicone has a viscosity of from about 1,000 cs to about 100,000 cs, more preferably from about 2,000 cs to about 50,000 cs, more preferably from about 4,000 cs to about 40,000 cs, and still more preferably from about 6,000 cs to about 30,000 cs.

The aminosilicone is contained in the composition of the present invention at a level by weight of from about 0.05% to about 20%, preferably from about 0.1% to about 10%, and more preferably from about 0.3% to about 5%.

Examples of preferred aminosilicones for use in embodiments of the subject invention include, but are not limited to, those which conform to the general formula (I):

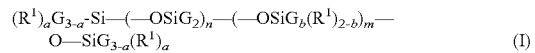

wherein G is hydrogen, phenyl, hydroxy, or $C_1$-$C_8$ alkyl, preferably methyl; a is 0 or an integer having a value from 1 to 3, preferably 1; b is 0, 1, or 2, preferably 1; wherein when a is 0, b is not 2; n is a number from 0 to 1,999; m is an integer from 0 to 1,999; the sum of n and m is a number from 1 to 2,000; a and m are not both 0; $R^1$ is a monovalent radical conforming to the general formula $CqH_{2q}L$, wherein q is an integer having a value from 2 to 8 and L is selected from the following groups: $-N(R^2)CH_2-CH_2-N(R^2)_2$; $-N(R^2)_2$; $-N(R^2)^+_3A^-$; $-N(R^2)CH_2-CH_2-N R^2H_2A^-$; wherein $R^2$ is hydrogen, phenyl, benzyl, or a saturated hydrocarbon radical, preferably an alkyl radical from about $C_1$ to about $C_{20}$; $A^-$ is a halide ion.

Highly preferred aminosilicones are those corresponding to formula (I) wherein m=0, a=1, q=3, G=methyl, n is preferably from about 1500 to about 1700, more preferably about 1600; and L is $-N(CH_3)_2$ or $-NH_2$, more preferably $-NH_2$. Other highly preferred aminosilicones are those corresponding to formula (I) wherein m=0, a=1, q=3, G=methyl, n is preferably from about 400 to about 600, more preferably about 500; and L is $-N(CH_3)_2$ or $-NH_2$, more preferably $-NH_2$. These aminosilicones can be called as terminal aminosilicones, as one or both ends of the silicone chain are terminated by nitrogen containing group.

An exemplary aminosilicone corresponding to formula (I) is the polymer known as "trimethylsilylamodimethicone", which is shown below in formula (II):

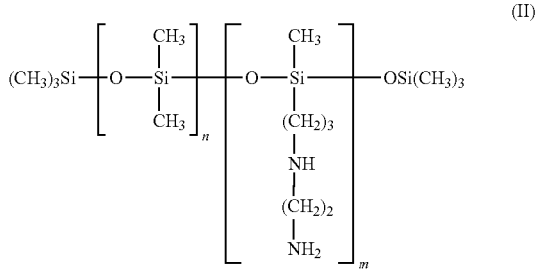

(II)

wherein n is a number from 1 to 1,999 and m is a number from 1 to 1,999.

c. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane) (methyl-vinylsiloxane) copolymer and mixtures thereof.

d. High Refractive Index Silicones

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

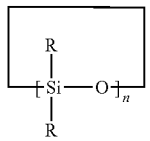

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described herein. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, preferably at least about 20%, more preferably at least about 25%, even more preferably at least about 35%, more preferably at least about 50%. Typically, the degree of aryl substitution will be less than about 90%, more generally less than about 85%, preferably from about 55% to about 80%.

Preferred high refractive index polysiloxane fluids have a combination of phenyl or phenyl derivative substituents (more preferably phenyl), with alkyl substituents, preferably $C_1$-$C_4$ alkyl (more preferably methyl), hydroxy, or $C_1$-$C_4$ alkylamino (especially —$R^1$NHR$^2$NH2 wherein each $R^1$ and $R^2$ independently is a $C_1$-$C_3$ alkyl, alkenyl, and/or alkoxy).

When high refractive index silicones are used in the compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present invention are disclosed in U.S. Pat. Nos. 2,826,551, 3,964,500, 4,364,837, British Pat. No. 849,433, and Silicon Compounds, Petrarch Systems, Inc. (1984).

e. Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

f. Modified Silicones or Silicone Copolymers

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes disclosed in German Patent No. DE 10036533; silicone aminopolyalkyleneoxide block copolymers disclosed in U.S. Pat. Nos. 5,807,956 and 5,981,681; hydrophilic silicone emulsions disclosed in U.S. Pat. No. 6,207,782; and polymers made up of one or more crosslinked rake or comb silicone copolymer segments disclosed in WO2004/062634. Additional modified silicones or silicone copolymers useful herein are described in WO2007/136708 and WO2006/022712.

In alternative embodiments of the present invention, the above-noted silicone-based quaternary ammonium compounds may be combined with the silicone polymers described in patent application numbers WO2002010259 and WO2002010257 and WO06138201A2.

2. Organic Conditioning Oils

The conditioning component of the compositions of the present invention may also comprise from about 0.05% to about 3%, preferably from about 0.08% to about 1.5%, more preferably from about 0.1% to about 1%, of at least one organic conditioning oil as the conditioning agent, either alone or in combination with other conditioning agents, such as the silicones (described herein).

a. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation. The concentration of such hydrocarbon oils in the composition preferably range from about 0.05% to about 20%, more preferably from about 0.08% to about 1.5%, and even more preferably from about 0.1% to about 1%.

b. Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

c. Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. monoesters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearoyl stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acids, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, 3. Other Conditioning Agents Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586 (Clairol), 4,507,280 (Clairol), 4,663,158 (Clairol), 4,197,865 (L'Oreal), 4,217,914 (L'Oreal), 4,381,919 (L'Oreal), and 4,422,853 (L'Oreal).

H. Anti-Dandruff Actives

The compositions of the present invention may also contain an anti-dandruff agent. Suitable, non-limiting examples of anti-dandruff particulates include: pyridinethione salts, azoles, selenium sulfide, particulate sulfur, and mixtures thereof. Preferred are pyridinethione salts. Such anti-dandruff particulate should be physically and chemically compatible with the essential components of the composition, and should not otherwise unduly impair product stability, aesthetics or performance.

1. Pyridinethione Salts

Pyridinethione anti-dandruff particulates, especially 1-hydroxy-2-pyridinethione salts, are highly preferred particulate anti-dandruff agents for use in compositions of the present invention. The concentration of pyridinethione anti-dandruff particulate typically ranges from about 0.1% to about 4%, by weight of the composition, preferably from about 0.1% to about 3%, more preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form, wherein the particles have an average size of up to about 20µ, preferably up to about 5µ, more preferably up to about 2.5µ. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters. Some preferred synthetic esters conform to the general Formula (IX):

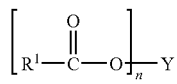

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

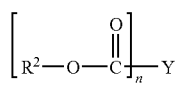

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

Specific non-limiting examples of suitable synthetic fatty esters for use in the compositions of the present invention include: P-43 ($C_8$-$C_{10}$ triester of trimethylolpropane), MCP-684 (tetraester of 3,3diethanol-1,5pentadiol), MCP 121 ($C_8$-$C_{10}$ diester of adipic acid), all of which are available from Mobil Chemical Company. .

2. Other Anti-microbial Actives

In addition to the anti-dandruff active selected from polyvalent metal salts of pyrithione, the present invention may further comprise one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Preferred anti-microbials include itraconazole, ketoconazole, selenium sulphide and coal tar.

a. Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein is ketoconazole.

b. Selenium Sulfide

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 µm, as measured by forward laser light scattering device (e.g. Malvern 3600 instrument), preferably less than 10 µm. Selenium sulfide compounds are described, for example, in U.S. Pat. Nos. 2,694,668; 3,152,046; 4,089,945; and 4,885,107.

c. Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

d. Keratolytic Agents

The present invention may further comprise one or more keratolytic agents such as Salicylic Acid.

e. Additional Anti-microbial Actives

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof. These actives, when used herein, are used at levels of from about 1% to about 4%, preferably from about 2% to about 4%.

I. Humectant

The compositions of the present invention may contain a humectant. The humectants herein are selected from the group consisting of polyhydric alcohols, water soluble alkoxylated nonionic polymers, and mixtures thereof. The humectants, when used herein, are preferably used at levels of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

J. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, preferably from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin R available from Rheox, Inc. Long chain acyl derivatives, ethylene glycol esters of long chain carboxylic acids, long chain amine oxides, and alkanol amides of long chain carboxylic acids in addition to the preferred materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

K. Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thioindigoid, quinacridone, phthalocianine, botanical, natural colors, including: water soluble components such as those having C. I. Names. The compositions of the present invention may also contain antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

The compositions of the present invention may also contain chelating agents.

Method of Making Shampoo Formulations

Any suitable method of making the shampoo of the present invention may be used. In one embodiment, undecyl-based surfactant is blended with the other components of the shampoo compositions, according to standard methods known in the art. The typical procedure used for a clarifying shampoo would be to combine the undecyl sulfate paste or undeceth sulfate paste or mixtures thereof with water, add the desired water soluble co-surfactant and finish the composition by the addition preservatives, pH control agents, perfume, and salts to obtain the target physical properties. If a water insoluble co-surfactant is desired the surfactant and water mixture can be heated to a suitable temperature to facilitate its incorporation. If a rheology modifier is desired it can be added to the surfactant mixture prior the finishing step.

In the case of conditioning shampoos, typically the surfactant paste is combined with the co-surfactant as above and diluted with water to a target level commensurate to achieving the final activity. Rheology modifiers can be added at this point followed by conditioning agents, e.g. sucrose polyesters, silicones or silicone emulsions or other oils, cationic polymers from polymer premixes, perfumes, pearlizing agents or opacifiers, perfumes, and preservatives. Appropriate mixing steps to insure homogeneity are used as needed. The product is finished by the addition of pH control agents, hydrotropes, and salts to the desired physical properties.

III. Compact Formulations

The sucrose polyesters of the present invention can also be used in a compact hair care formulation. A compact formula is a formula which delivers the same benefit to the consumer at a lower usage level. Compact formulations and methods of making compact formulations are described in U.S. Patent Provisional Application Ser. No. 61/011,631 filed Jan. 18, 2008.

Method of Making Compact Formulations

In order to get to the surfactant active levels for the products that use ⅓ the typical shampoo weight or volume level there is a need to use one or more of the components that are derived from higher activity lamellar phase pastes. These materials can include, but are not limited to, SLE(1)S, C11E(1)S, C13-15 paraffin sulfonate, as flowable fluids. Higher activity isotropic pastes of C11S (35%) and SLS containing an enriched level of C10 (38%) can be made to facilitate these formulations as well. In a typical procedure the isotropic paste can be combined with the co-surfactant, preservatives, and the desired quantity of lamellar phase paste. This can be mixed on a Flak Tek speed mixer until uniform. Pearlizer dispersion (EGDS), cationic polymer, and perfume are added and mixed again until a uniform mixture is achieved. Finally, surcrose polyesters, silicone emulsion, additional preservatives and pH control agents are mixed in with more gentle agitation to achieve the desired final product mixture.

IV. Conditioner Formulations

Conditioner formulations of the present invention incorporate the sucrose polyesters of the present invention described above via either pre-emulsification or crystallization in-situ at different cooling rates from a hot melt formulation. The conditioner formulations comprise sucrose polyester particles of a size from about 0.5 to about 100 microns. Conditioner formulations may further comprise one or more of the following optional ingredient(s).

Conditioner Formulation Optional Ingredients
A. Cationic Surfactant System

The composition of the present invention comprises a cationic surfactant system. The cationic surfactant system can be one cationic surfactant or a mixture of two or more cationic surfactants. The cationic surfactant system is included in the composition at a level by weight of from about 0.1% to about 10%, preferably from about 0.5% to about 8%, more preferably from about 1% to about 5%, still more preferably from about 1.4% to about 4%, in view of balance among ease-to-rinse feel, rheology and wet conditioning benefits.

A variety of cationic surfactants including mono- and dialkyl chain cationic surfactants can be used in the compositions of the present invention. Among them, preferred are mono-alkyl chain cationic surfactants in view of providing desired gel matrix and wet conditioning benefits. The mono-alkyl cationic surfactants are those having one long alkyl chain which has from 12 to 22 carbon atoms, preferably from 16 to 22 carbon atoms, more preferably C18-22 alkyl group, in view of providing balanced wet conditioning benefits. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. Such mono-alkyl cationic surfactants include, for example, mono-alkyl quaternary ammonium salts and mono-alkyl amines. Mono-alkyl quaternary ammonium salts include, for example, those having a non-functionalized long alkyl chain. Mono-alkyl amines include, for example, mono-alkyl amidoamines and salts thereof.

Mono-long alkyl quaternized ammonium salts useful herein are those having the formula (II):

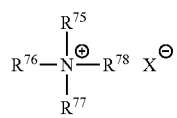

(II)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g. those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 22 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Examples of preferred mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt. Among them, highly preferred are behenyl trimethyl ammonium salt and stearyl trimethyl ammonium salt.

Mono-alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Although the mono-alkyl chain cationic surfactants are preferred, other cationic surfactants such as di-alkyl chain cationic surfactants may also be used alone, or in combination with the mono-alkyl chain cationic surfactants. Such di-alkyl chain cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

B. High Melting Point Fatty Compound

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g. some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

The high melting point fatty compound is included in the composition at a level of from about 0.1% to about 40%, preferably from about 1% to about 30%, more preferably from about 1.5% to about 16% by weight of the composition, from about 1.5% to about 8% in view of providing improved conditioning benefits such as slippery feel during the application to wet hair, softness and moisturized feel on dry hair.

C. Aqueous Carrier

The conditioning composition of the present invention comprises an aqueous carrier. The level and species of the carrier are selected according to the compatibility with other components, and other desired characteristic of the product. Generally, the compositions of the present invention comprise from about 20% to about 99%, preferably from about 30% to about 95%, and more preferably from about 80% to about 95% water.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product.

D. Gel Matrix

Preferably, the above cationic surfactants, together with high melting point fatty compounds and an aqueous carrier, form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

E. Silicone Compound

Preferably, the compositions of the present invention contain a silicone compound. It is believed that the silicone compound can provide smoothness and softness on dry hair. The silicone compounds herein can be used at levels by weight of the composition of preferably from about 0.1% to about 20%, more preferably from about 0.15% to about 10%, still more preferably from about 0.2% to about 8%.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferably, the silicone compounds have an average particle size of from about 1 microns to about 50 microns, in the composition. Preferably, silicone compounds useful herein include amino substituted materials.

Compositions of the present invention include an aminosilicone. Aminosilicones, as provided herein, are silicones containing at least one primary amine, secondary amine, tertiary amine, or a quaternary ammonium group. Preferred aminosilicones may have less than about 0.5% nitrogen by weight of the aminosilicone, more preferably less than about 0.2%, more preferably still, less than about 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present invention.

Preferably, the aminosilicones used in the present invention have a particle size of less than about 50μ once incorporated into the final composition. The particle size measurement is taken from dispersed droplets in the final composition. Particle size may be measured by means of a laser light scattering technique, using a Horiba model LA-910 Laser Scattering Particle Size Distribution Analyzer (Horiba Instruments, Inc.).

In one of the preferred embodiments, the aminosilicone has a viscosity of from about 1,000 cs (centistokes) to about 1,000,000 cs, more preferably from about 10,000 cs to about 700,000 cs, more preferably from about 50,000 cs to about 500,000 cs, and still more preferably from about 100,000 cs to about 400,000 cs. This embodiment may also comprises a low viscosity fluid, such as, for example, those materials described below in Section F. (1). The viscosity of aminosilicones discussed herein is measured at 25° C.

In another preferred embodiment, the aminosilicone has a viscosity of from about 1,000 cs to about 100,000 cs, more preferably from about 2,000 cs to about 50,000 cs, more preferably from about 4,000 cs to about 40,000 cs, and still more preferably from about 6,000 cs to about 30,000 cs.

The aminosilicone is contained in the composition of the present invention at a level by weight of from about 0.05% to about 20%, preferably from about 0.1% to about 10%, and more preferably from about 0.3% to about 5%.

Examples of preferred aminosilicones for use in embodiments of the subject invention include, but are not limited to, those which conform to the general formula (I):

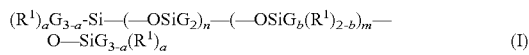

wherein G is hydrogen, phenyl, hydroxy, or $C_1$-$C_8$ alkyl, preferably methyl; a is 0 or an integer having a value from 1 to 3, preferably 1; b is 0, 1, or 2, preferably 1; wherein when a is 0, b is not 2; n is a number from 0 to 1,999; m is an integer from 0 to 1,999; the sum of n and m is a number from 1 to 2,000; a and m are not both 0; $R^1$ is a monovalent radical conforming to the general formula $C_qH_{2q}L$, wherein q is an integer having a value from 2 to 8 and L is selected from the following groups: —N($R^2$)$CH_2$—$CH_2$—N($R^2$)$_2$; —N($R^2$)$_2$; —N($R^2$)$^+_3$$A^-$; —N($R^2$)$CH_2$—$CH_2$—N $R^2H_2A^-$; wherein $R^2$ is hydrogen, phenyl, benzyl, or a saturated hydrocarbon radical, preferably an alkyl radical from about $C_1$ to about $C_{20}$; $A^-$ is a halide ion.

Highly preferred aminosilicones are those corresponding to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Other highly preferred aminosilicones are those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. These aminosilicones can be called as terminal aminosilicones, as one or both ends of the silicone chain are terminated by nitrogen containing group.

An exemplary aminosilicone corresponding to formula (I) is the polymer known as "trimethylsilylamodimethicone", which is shown below in formula (II):

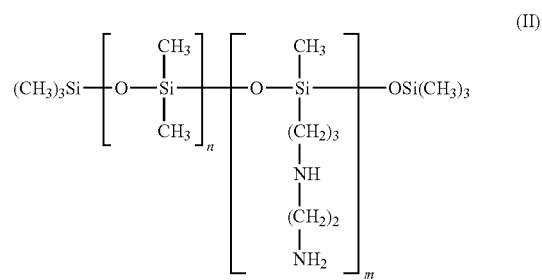

wherein n is a number from 1 to 1,999 and m is a number from 1 to 1,999.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

The other silicone compounds useful herein include polyalkyl or polyaryl siloxanes with the following structure:

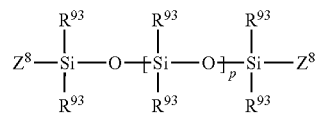

wherein $R^{93}$ is alkyl or aryl, and p is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The other silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

The silicone compounds may further be incorporated in the present composition in the form of an emulsion, wherein the emulsion is made by mechanical mixing, or in the stage of synthesis through emulsion polymerization, with or without the aid of a surfactant selected from anionic surfactants, non-ionic surfactants, cationic surfactants, and mixtures thereof.

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes disclosed in German Patent No. DE 10036533; silicone aminopolyalkyleneoxide block copolymers disclosed in U.S. Pat. Nos. 5,807,956 and 5,981,681; hydrophilic silicone emulsions disclosed in U.S. Pat. No. 6,207,782; and polymers made up of one or more crosslinked rake or comb silicone copolymer segments disclosed in WO2004/062634. Additional modified silicones or silicone copolymers useful herein are described in WO2007/136708 and WO2006/022712.

In alternative embodiments of the present invention, the above-noted silicone-based quaternary ammonium compounds may be combined with the silicone polymers described in patent application numbers WO2002010259 and WO2002010257 and WO06138201A2.

F. Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: cationic conditioning polymers including, for example, cationic celluloses such as polyquaternium-10, and cationic guar gums; additional cationic surfactant including, for example, monoalkyl quaternized ammonium salts such as behenyl trimethyl ammonium chloride and dialkyl quaternized ammonium salt such as dicetyldimethyl ammonium chloride; low melting point oils having a melting point of less than 25° C. including, for example, unsaturated fatty alcohols such as oleyl alcohol and ester oils such as pentaerythritol ester oils; polyethylene glycols; other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and Phenoxyethanol; pH adjusting agents, such as citric acid, sodium citrate, succinic acid, phosphoric acid, sodium hydroxide, sodium carbonate; salts, in general, such as potassium acetate and sodium chloride; perfumes; sequestering agents, such as ethylenediamine tetra acetic acid and its salts; and ultraviolet and infrared screening and absorbing agents such as octyl salicylate, octyl methoxycinnamate, benzophenone-3 and benzophenone-4.

Product Forms

The conditioning compositions of the present invention can be in the form of rinse-off products or leave-on products, and can be formulated in a wide variety of product forms, including but not limited to creams, gels, emulsions, mousses and sprays.

The conditioning composition of the present invention is especially suitable for rinse-off hair conditioner. Such compositions are preferably used by following steps:
(i) after shampooing hair, applying to the hair an effective amount of the conditioning compositions for conditioning the hair; and
(ii) then rinsing the hair.

Test Methods

G' and G" Test Method

This method provides a G' and G" value for a given sucrose polyester blend composition. Each blend is carefully transferred to a rheometer plate while avoiding applying vigorous shear to each blend composition.

A suitable rheometer for use in the present method is the Haake RS-150 RheoStress Rheometer interfaced with a computer having suitable software that provides data recordation and analysis. The test is performed at temperature of 35° C. and the equilibration time is 3 minute. The rheometer is configured with a 35 mm diameter, 4 degree steel cone at a gap setting to the plate of 140 μm as measured from the center of the cone. The angular frequency is applied, starting at 0.01 Hz, where G' and G" are measured three times and the average of G' and G" are recorded by the software. Similarly, these measurements are repeated at each decade after 0.01 Hz and up to 100 Hz. All measurements were performed at a constant stress of 1 Pa.

Wet and Dry Conditioning Test Method

This test method is designed to allow for a subjective evaluation of the basic performance of conditioning shampoos for both wet combing and dry combing efficacy. The control treatments are a clarifying shampoo that employs only surfactants and has no conditioning materials present and this same shampoo used in the washing process followed by the application of a mid-range hair conditioner. These treatments allow for easy differentiation of performance of a set prototype conditioning shampoos. In a typical test 3 to 5 separate formulations can be assessed for their performance. The substrate is virgin brown hair obtainable from a variety of sources that is screened to insure uniformity and lack of meaningful surface damage.

Treatment Procedure

Five 4 gram, 8 inch length switches are combined in a hair switch holder, wet for ten seconds with manipulation with water at 40 C and typical hardness (9-10 gpg) to insure complete and even wetting. The switch is deliquored lightly and product is applied uniformly over the length of the combined switches from one inch below the holder towards the end at a level of 0.1 g product per one gram of dry hair (0.1 g/g of hair or 2 g for 20 g hair). For more concentrated prototypes the usage level is reduced to 0.05 g/g of hair. The switch combo is lathered by a rubbing motion typical of that used by consumers for 30 seconds and rinsed with water flowing at 1.5 gal/min. at 40 C (with the hair being manipulated) to insure completeness for 30 seconds. This step is repeated. On the switch combo where conditioner is applied, it is applied in the same way as shampoo above, manipulated throughout the switch combo and rinsed thoroughly with manipulation. The switches are deliquored lightly, separated from each other, hung on a rack so that they are not in contact and detangled with a wide tooth comb.

Grading Procedures

For wet combing evaluations using trained graders, the switches are separated on the rack into the five sets with one switch from each treatment included in the grading set. Only two combing evaluations are performed on each switch. The graders are asked to compare the treatments by combing with a narrow tooth nylon comb typical of those used by consumers and rate the ease/difficulty on a zero to ten scale. Ten separate evaluations are collected and the results analyzed by a statistical analysis package for establishing statistical significance. Control charting is regularly used to insure that the low and high controls separate into their regular domains. Statistical significance in differences between treatments is determined using Statgraphics Plus 5.1. All conditioning prototypes must be more than two LSDs above the clarifying control to be viewed as acceptable.

For dry combing evaluations, the switches from above are moved into a controlled temperature and humidity room (72 F/50% RH) and allowed to dry overnight. They remain separated as above and panelists are requested to evaluate dry conditioning performance by making three assessments; dry combing ease of the middle of the switch, dry combing ease of the tips, and a tactile assessment of tip feel. The same ten point scale is used for these comparisons. Again, only two panelists make an assessment of each switch set. Statistical analysis to separate differences is done using the same method as above.

NON-LIMITING EXAMPLES

The hair care compositions illustrated in the following Examples illustrate specific embodiments of the compositions of the present invention, but are not intended to be limiting thereof. Other modifications can be undertaken by the skilled artisan without departing from the spirit and scope of this invention. These exemplified embodiments of the shampoo composition of the present invention provide enhanced cleansing benefits to the hair.

The hair care compositions illustrated in the following Examples are prepared by conventional formulation and mixing methods. All exemplified amounts are listed as weight percents and exclude minor materials such as diluents, preservatives, color solutions, imagery ingredients, botanicals, and so forth, unless otherwise specified. All percentages are based on weight unless otherwise specified.

A. Shampoo Examples

The Shampoo Examples can be prepared using the following method:

To prepare 1000 g of shampoo containing 2% sefose a 1L vessel is fitted with large variable speed paddle stirrer. Throughout the preparation the product is stirred just enough to give good mixing without entraining large quantities of air.

(1) Add 618.5 g water, (2) Add 120 g 30% active w/w SLE(3)S, (3) Add 240 g 30% active w/w SLS, (5) Add 1.5 g Enhance 3270 Polymer (6) Raise temperature to 74° C. with continued stirring (7) Add 20 g active Sefose raw material Maintain temperature at 65 Deg. C. for 30 mins. Then cool to room temperature under ambient conditions.

| Ingredient | No Silicone | | | | | | |
| --- | --- | --- | --- | --- | --- | --- | --- |
| | 1 | 2 | 3 | 4 | 5 | 6 | 7 |
| Water | q.s. | q.s. | q.s. | q.s. | q.s. | q.s. | q.s. |
| Catonic Guar[1] | 0.25 | — | — | — | 0.1 | — | — |
| Cationic *Cassia*[2] | — | 0.25 | — | — | 0.1 | 0.3 | 0.3 |
| PQ-10[3] | — | — | 0.25 | — | — | — | — |
| PQ-76[4] | — | — | — | 0.25 | — | — | — |
| Sodium Laureth Sulfate[5] | 8.5 | 15.0 | 10.0 | 6.0 | 8.5 | 10.0 | 10.0 |
| Sodium Lauryl Sulfate[6] | 6.5 | — | 6.0 | 5.0 | 6.5 | 3.0 | 3.0 |
| CMEA[7] | 0.8 | 1.0 | 0.8 | 0.8 | 1.0 | 0.8 | 0.8 |
| Cocoamidopropyl Betaine[8] | 2.0 | 3.0 | — | 0.75 | 2.0 | 3.5 | 3.5 |
| Sefose[9] | 2.0 | 2.0 | 2.0 | 2.0 | 2.0 | — | — |
| Sefose[10] | — | — | — | — | — | 2.0 | — |
| Sefose[11] | — | — | — | — | — | — | 2.0 |
| Glycerine[12] | — | 1.0 | — | — | 0.5 | 1.0 | — |

|  | No Silicone | | | | | | |
|---|---|---|---|---|---|---|---|
| Ingredient | 1 | 2 | 3 | 4 | 5 | 6 | 7 |
| Fragrance | 0.70 | 0.70 | 0.70 | 0.70 | 0.70 | 0.70 | 0.70 |
| Preservatives, pH, viscosity adjustment | Up to 3% | Up to 3% | Up to 3% | Up to 3% | Up to 3% | Up to 3% | Up to 3% |

[1] Jaguar Excel, from Rhodia
[2] Cationic Cassia, MW = 300,000; 4.25% Nitrogen, from Lubrizol Advanced Materials
[3] LR 400, from Amerchol
[4] Mirapol AT-1, from Rhodia
[5] Sodium Laureth Sulfate, from P&G
[6] Sodium Lauryl Sulfate, from P&G
[7] Ninol Comf, from Stepan
[8] Amphosol HCA-B, from Stepan
[9] Sefose-1618H, IV = 3, IBAR = 7.8, from P&G
[10] Sefose-2275C, IV = 5, IBAR = 8, from P&G
[11] Sefose-1618S, IV = 85, IBAR = 6, from P&G
[12] Superol V Glycerine USP, from P&G

|  | Examples with 30 nm silicone particles | | | | | | |
|---|---|---|---|---|---|---|---|
| Ingredient | 8 | 9 | 10 | 11 | 12 | 13 | 14 |
| Water | q.s. | q.s. | q.s. | q.s. | q.s. | q.s. | q.s. |
| Catonic Guar[1] | 0.25 | — | — | — | 0.1 | — | — |
| Cationic Cassia[2] | — | 0.25 | — | — | 0.1 | 0.3 | 0.3 |
| PQ-10[3] | — | — | 0.25 | — | — | — | — |
| PQ-76[4] | — | — | — | 0.25 | — | — | — |
| Sodium Laureth Sulfate[5] | 8.5 | 15.0 | 10.0 | 6.0 | 8.5 | 10.0 | 10.0 |
| Sodium Lauryl Sulfate[6] | 6.5 | — | 6.0 | 5.0 | 6.5 | 3.0 | 3.0 |
| CMEA[7] | 0.8 | 1.0 | 0.8 | 0.8 | 1.0 | 0.8 | 0.8 |
| Cocoamidopropyl Betaine[8] | 2.0 | 3.0 | — | 0.75 | 2.0 | 3.5 | 3.5 |
| Sefose[9] | 2.0 | 2.0 | 2.0 | 2.0 | 2.0 | — | 1.0 |
| Sefose[10] | — | — | — | — | — | 2.0 | — |
| Sefose[11] | — | — | — | — | — | — | 1.0 |
| Glycerine[12] | — | 1.0 | — | — | 0.5 | 1.0 | — |
| Silicone Microemulsion[13] | 0.5 | 0.5 | 0.5 | 0.25 | 0.2 | 0.4 | 0.25 |
| Aminosilicone[14] | — | — | — | — | — | — | 0.5 |
| Fragrance | 0.70 | 0.70 | 0.70 | 0.70 | 0.70 | 0.70 | 0.70 |
| Preservatives, pH, viscosity adjustment | Up to 3% | Up to 3% | Up to 3% | Up to 3% | Up to 3% | Up to 3% | Up to 3% |

[1] Jaguar Excel, from Rhodia
[2] Cationic Cassia, MW = 300,000; 4.25% Nitrogen, from Lubrizol Advanced Materials
[3] LR 400, from Amerchol
[4] Mirapol AT-1, from Rhodia
[5] Sodium Laureth Sulfate, from P&G
[6] Sodium Lauryl Sulfate, from P&G
[7] Ninol Comf, from Stepan
[8] Amphosol HCA-B, from Stepan
[9] Sefose-1618H, IV = 3, IBAR = 7.8, from P&G
[10] Sefose-2275C, IV = 5, IBAR = 8, from P&G
[11] Sefose-1618S, IV = 85, IBAR = 6, from P&G
[12] Superol V Glycerine USP, from P&G
[13] DC-1870 from Dow Corning
[14] DC 2-8194 from Dow Corning

|  | Examples with 300 nm silicone particles | | | | | | |
|---|---|---|---|---|---|---|---|
| Ingredient | 15 | 16 | 17 | 18 | 19 | 20 | 21 |
| Water | q.s. | q.s. | q.s. | q.s. | q.s. | q.s. | q.s. |
| Catonic Guar[1] | 0.25 | — | — | — | 0.1 | — | — |
| Cationic Cassia[2] | — | 0.25 | — | — | 0.1 | 0.3 | 0.3 |
| PQ-10[3] | — | — | 0.25 | — | — | — | — |
| PQ-76[4] | — | — | — | 0.25 | — | — | — |
| Sodium Laureth Sulfate[5] | 8.5 | 15.0 | 10.0 | 6.0 | 8.5 | 10.0 | 10.0 |
| Sodium Lauryl Sulfate[6] | 6.5 | — | 6.0 | 5.0 | 6.5 | 3.0 | 3.0 |
| CMEA[7] | 0.8 | 1.0 | 0.8 | 0.8 | 1.0 | 0.8 | 0.8 |
| Cocoamidopropyl Betaine[8] | 2.0 | 3.0 | — | 0.75 | 2.0 | 3.5 | 3.5 |
| Sefose[9] | 2.0 | 2.0 | 2.0 | 2.0 | 2.0 | — | 1.0 |
| Sefose[10] | — | — | — | — | — | 2.0 | — |
| Sefose[11] | — | — | — | — | — | — | 1.0 |
| Glycerine[12] | — | 1.0 | — | — | 0.5 | 1.0 | — |
| Dimethicone Emulsion[13] | 1.0 | 1.5 | 1.0 | 1.0 | 2.0 | 1.0 | — |
| Aminosilicone[14] | — | — | — | — | — | — | 2.0 |
| Ethylene Glycol Distearate[15] | 1.5 | 1.5 | 1.5 | 1.5 | 1.5 | 1.5 | 1.5 |
| Fragrance | 0.70 | 0.70 | 0.70 | 0.70 | 0.70 | 0.70 | 0.70 |
| Preservatives, pH, viscosity adjustment | Up to 3% | Up to 3% | Up to 3% | Up to 3% | Up to 3% | Up to 3% | Up to 3% |

[1] Jaguar Excel, from Rhodia
[2] Cationic Cassia, MW = 300,000; 4.25% Nitrogen, from Lubrizol Advanced Materials
[3] LR 400, from Amerchol
[4] Mirapol AT-1, from Rhodia
[5] Sodium Laureth Sulfate, from P&G
[6] Sodium Lauryl Sulfate, from P&G
[7] Ninol Comf, from Stepan
[8] Amphosol HCA-B, from Stepan
[9] Sefose-1618H, IV = 3, IBAR = 7.8, from P&G
[10] Sefose-2275C, IV = 5, IBAR = 8, from P&G
[11] Sefose-1618S, IV = 85, IBAR = 6, from P&G
[12] Superol V Glycerine USP, from P&G
[13] DC-1664 from Dow Corning
[14] Silicone; terminal aminopropyl substitution, visc. 350,000, D = 1600, M' = 2, particle size = 3 μm from Momentive
[15] EGDS Pure, from Degussa Goldschmidt

|  | Examples with 30 micron silicone particles | | | | | | |
|---|---|---|---|---|---|---|---|
| Ingredient | 22 | 23 | 24 | 25 | 26 | 27 | 28 |
| Water | q.s. | q.s. | q.s. | q.s. | q.s. | q.s. | q.s. |
| Catonic Guar[1] | 0.25 | — | — | — | 0.1 | — | — |
| Cationic Cassia[2] | — | 0.25 | — | — | 0.1 | 0.3 | 0.3 |
| PQ-10[3] | — | — | 0.25 | — | — | — | — |
| PQ-76[4] | — | — | — | 0.25 | — | — | — |
| Sodium Laureth Sulfate[5] | 8.5 | 10.0 | 10.0 | 6.0 | 8.5 | 10.0 | 10.0 |
| Sodium Lauryl Sulfate[6] | 6.5 | 4.0 | 6.0 | 5.0 | 6.5 | 3.0 | 3.0 |
| CMEA[7] | 0.8 | 1.0 | 0.8 | 0.8 | 1.0 | 0.8 | 0.8 |
| Cocoamidopropyl Betaine[8] | 2.0 | 2.0 | — | 0.75 | 2.0 | 3.5 | 3.5 |
| Sefose[9] | 2.0 | 2.0 | 2.0 | 2.0 | 2.0 | — | — |
| Sefose[10] | — | — | — | — | — | 2.0 | — |
| Sefose[11] | — | — | — | — | — | — | 2.0 |
| Glycerine[12] | — | 1.0 | — | — | 0.5 | 1.0 | — |
| Dimethicone Gum[13] | 1.0 | 1.25 | 2.0 | 1.0 | 1.5 | 3.5 | 2.5 |
| Ethylene Glycol Distearate[14] | 1.5 | 1.5 | 1.5 | 1.5 | 1.5 | 1.5 | 1.5 |

-continued

Examples with 30 micron silicone particles

| Ingredient | 22 | 23 | 24 | 25 | 26 | 27 | 28 |
|---|---|---|---|---|---|---|---|
| Fragrance | 0.70 | 0.70 | 0.70 | 0.70 | 0.70 | 0.70 | 0.70 |
| Preservatives, pH, viscosity adjustment | Up to 3% | Up to 3% | Up to 3% | Up to 3% | Up to 3% | Up to 3% | Up to 3% |

[1]Jaguar Excel, from Rhodia
[2]Cationic *Cassia*, MW = 300,000; 4.25% Nitrogen, from Lubrizol Advanced Materials
[3]LR 400, from Amerchol
[4]Mirapol AT-1, from Rhodia
[5]Sodium Laureth Sulfate, from P&G
[6]Sodium Lauryl Sulfate, from P&G
[7]Ninol Comf, from Stepan
[8]Amphosol HCA-B, from Stepan
[9]Sefose-1618H, IV = 3, IBAR = 7.8, from P&G
[10]Sefose-2275C, IV = 5, IBAR = 8, from P&G
[11]Sefose-1618S, IV = 85, IBAR = 6, from P&G
[12]Superol V Glycerine USP, from P&G
[13]Viscasil 330M, from Momentive
[14]EGDS Pure, from Degussa Goldshmidt

B. Compact Examples (Shampoo)

| Ingredient | Weight % |
|---|---|
| SLE1S | 12.4 |
| SLE1s (conc 70%) | 4.0 |
| CB | 2.2 |
| C11S | 5.0 |
| N67S | 1.0 |
| EDTA | 0.1 |
| Sodium Citrate | 0.4 |
| NA EGDS mix | 1.25 |
| Kathon CG | 0.00005 |
| Citric Acid | pH 5.5-6.5 |

| Ingredient | Targ. wt % |
|---|---|
| SLE1S | 12.400 |
| SLE1S (conc 70%) | 4.000 |
| CB | 2.200 |
| C11S | 5.000 |
| N67S | 1.000 |
| EDTA | 0.100 |
| Sodium Citrate | 0.400 |
| Na EGDS mix | 1.250 |
| Kathon CG | 0.00005 |
| Citric Acid | pH 5.5-6.5 |

C. Conditioner Examples

Leave On Conditioner Examples

| | A % | B % | C % |
|---|---|---|---|
| Pure water (cold) | 32.000 | 32.000 | 32.000 |
| Hydroxyethyl Cellulose | 0.150 | 0.150 | 0.150 |
| Polyox PEG-2M | 0.300 | 0.300 | 0.300 |
| Pure water | 59.875 | 60.975 | 60.025 |
| DTDMAC | 0.400 | 0.400 | 0.400 |
| Cetyl Alcohol | 0.300 | 0.450 | 0.300 |
| Stearyl Alcohol | 0.150 | 0.250 | 0.150 |
| Sefose 1618H | 1.200 | 2.500 | 1.200 |
| Sefose 1618U | 0.150 | 0.500 | — |
| SAPDMA | 0.500 | 0.500 | 0.500 |
| Glyceryl Monostearate | 0.150 | 0.150 | 0.150 |
| Oleyl Alcohol | 0.150 | 0.150 | 0.150 |
| Benzyl Alcohol | 0.400 | 0.400 | 0.400 |
| Acid EDTA | 0.100 | 0.100 | 0.100 |
| Silicone Blend | 3.000 | — | 3.000 |
| Glydant | 0.360 | 0.360 | 0.360 |
| Citric Acid | 0.070 | 0.070 | 0.070 |
| Purified Water | 0.300 | 0.300 | 0.300 |
| Lysine Hydrochloride | 0.028 | 0.028 | 0.028 |
| L-Tyrosine Metyl Ester | 0.014 | 0.014 | 0.014 |
| Histidine | 0.008 | 0.008 | 0.008 |
| Panthenol | 0.045 | 0.045 | 0.045 |
| Perfume | 0.350 | 0.350 | 0.350 |
| | 100.0 | 100.0 | 100.0 |

In suitable container add water at top of ingredient list and at room temperature and with agitation and the hydroxyethyl cellulose. Disperse well and add Polyox PEG-2M slowly. Add the next portion of water. Place container on a suitable heat source and heat to 80 to 85 C while mixing. Add the cetyl and stearyl alcohols, Sefose 1618H and 1618 U, Polawax NF, DTDMAC, SAPDMA, glyceryl monostearate, oleyl and benzyl alcohols, and EDTA. Mix for 5 minutes and cool to 47 C. With continuous mixing add the silicone, Glydant, citric acid, all amino acids, panthenol and perfume. Pack product in an appropriate container.

Rinse-Off Conditioner Formulations:

| | | A % | B % | C % | D % | E % | F % | G % |
|---|---|---|---|---|---|---|---|---|
| Stage A | Water | 84.62 | 83.99 | 87.44 | 85.69 | 84.94 | 85.19 | 84.49 |
| | Sodium Carboxy Methyl Cellulose | — | — | 0.50 | — | 0.75 | — | — |
| | *Cassia* EX-906 Polymer | — | 0.20 | — | — | — | — | 0.20 |
| | Behenyl Trimethyl Ammonium Chloride | 2.85 | 2.85 | — | 2.85 | 2.85 | — | 2.85 |
| | Sodium Cetearyl Sulfate (Lanette E) | — | — | 2.00 | — | — | 2.50 | — |
| | Stearyl Alcohol | 4.64 | 4.64 | 4.64 | 4.64 | 1.50 | 4.50 | 4.64 |
| | Cetyl Alcohol | 1.86 | 1.86 | 1.86 | 1.86 | 0.50 | 2.00 | 1.86 |
| | Sefose 1618H IBAR = 8, IV = 3 | 3.57 | 2.00 | — | 1.00 | 3.00 | 3.00 | — |
| | Sefose 1618U IBAR = 8, IV = 135 | — | — | — | 0.50 | — | 0.50 | — |
| | Soybean Ester Oil | — | — | — | — | — | 2.00 | — |
| | EDTA | 0.13 | 0.13 | 0.13 | 0.13 | 0.13 | 0.13 | 0.13 |

-continued

|  |  | A % | B % | C % | D % | E % | F % | G % |
|---|---|---|---|---|---|---|---|---|
|  | Benzyl Alcohol | 0.40 | 0.40 | 0.40 | 0.40 | 0.40 | 0.40 | 0.40 |
|  | Sodium Hydroxide Solution (1%) | 1.40 | 1.40 | — | 1.40 | 1.40 | — | 1.40 |
|  | Kathon CG | 0.03 | 0.03 | 0.03 | 0.03 | 0.03 | 0.03 | 0.03 |
| Stage B | Silicone Fluids | — | 2.00 | — | 1.00 | 2.00 | — | 1.00 |
|  | Sefose 1618H IBAR = 8, IV = 3 | — | — | 2.00 | — | — | 1.00 | 2.00 |
|  | Sefose 1618U IBAR = 8, IV = 135 | — | — | 0.50 | — | — | 0.25 | 0.50 |
|  | Panthenol | 0.15 | 0.15 | 0.15 | 0.15 | 0.15 | 0.15 | 0.15 |
|  | Perfume | 0.35 | 0.35 | 0.35 | 0.35 | 0.35 | 0.35 | 0.35 |
|  | Total | 100.0 | 100.0 | 100.0 | 100.0 | 100.0 | 100.0 | 100.0 |

Equipment and Procedure:

In a suitable container weigh out the water in stage A. Heat water to approximately 80 to 85 C and with continuous stirring from a mixer introduce each component in order listed one at a time, ensuring the last one added completely dissolves or hydrates before adding the next one. Maintain temperature at the above specified range during and 5 minutes after the material addition in stage A. Ensure mixing provides good turn-over of product. With continuous stirring and good turn-over cool to 60 to 65 C. Add components in stage B in order listed. After adding the last component stir for 3 more minutes with a vigorous mixing. Cool to room temperature and store in an appropriate container.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care composition comprising:
   a) a conditioning active comprising a sucrose polyester blend; wherein the blend comprises two or more sucrose polyesters,
      i) at least one sucrose polyester has a melting point greater than about 30° C., an esterification (IBAR) of about 8, an iodine value (IV) of about 3, and
      ii) at least one sucrose polyester has an IBAR of about 8, and an IV of about 135, and
      iii) wherein the sucrose polyester blend has an IBAR of about 8 and an IV between about 3 and about 135; and
   b) an aqueous carrier.

2. The hair care composition of claim 1, wherein said composition further comprises a fatty alcohol having from about 14 to about 30 carbon atoms.

3. The composition of claim 1, wherein the hair care composition is selected from the group consisting of shampoos, conditioners, and hair styling products.

4. The hair care composition of claim 1, further comprising a surfactant.

5. The hair care composition of claim 1, further comprising a polymer.

6. The hair care composition of claim 5, wherein said polymer is cassia.

7. The hair care composition of claim 1, wherein said sucrose polyester is a particle, and the particle is a least about 0.05 microns.

8. The hair care composition of claim 7, wherein said sucrose polyester is a particle, and the particle is from about 0.5 to about 100 microns in size.

* * * * *